United States Patent
Garzon et al.

(10) Patent No.: US 7,264,700 B1
(45) Date of Patent: Sep. 4, 2007

(54) THIN FILM MIXED POTENTIAL SENSORS

(75) Inventors: Fernando H. Garzon, Santa Fe, NM (US); Eric L. Brosha, Los Alamos, NM (US); Rangachary Mukundan, Santa Fe, NM (US)

(73) Assignee: Los Alamos National Security, LLC, Los Alamos, NM (US)

( * ) Notice: Subject to any disclaimer, the term of this patent is extended or adjusted under 35 U.S.C. 154(b) by 481 days.

(21) Appl. No.: 10/760,924

(22) Filed: Jan. 20, 2004

(51) Int. Cl.
*G01N 27/407* (2006.01)

(52) U.S. Cl. .................... 204/426; 204/424; 204/192.1
(58) Field of Classification Search ................ 204/424, 204/426, 192.1; 205/783.5
See application file for complete search history.

(56) References Cited

U.S. PATENT DOCUMENTS

| | | | |
|---|---|---|---|
| 4,277,323 A | 7/1981 | Muller et al. | |
| 4,902,400 A | 2/1990 | Usami et al. | |
| 5,215,643 A * | 6/1993 | Kusanagi et al. | 204/412 |
| 5,755,940 A * | 5/1998 | Shindo | 204/424 |
| 6,352,631 B1 | 3/2002 | Bloemer et al. | |
| 6,605,202 B1 | 8/2003 | Mukundan et al. | |
| 6,656,336 B2 | 12/2003 | Mukundan et al. | |
| 2003/0075439 A1 * | 4/2003 | Dalmia et al. | 204/421 |

* cited by examiner

*Primary Examiner*—Kaj K. Olsen
(74) *Attorney, Agent, or Firm*—Ray G. Wilson; Holly L. Teeter

(57) ABSTRACT

A mixed potential sensor for oxidizable or reducible gases and a method of making. A substrate is provided and two electrodes are formed on a first surface of the substrate, each electrode being formed of a different catalytic material selected to produce a differential voltage between the electrodes from electrochemical reactions of the gases catalyzed by the electrode materials. An electrolytic layer of an electrolyte is formed over the electrodes to cover a first portion of the electrodes from direct exposure to the gases with a second portion of the electrodes uncovered for direct exposure to the gases.

12 Claims, 4 Drawing Sheets

THIN FILM MIXED POTENTIAL SENSORS

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates generally to gas sensors, and, more particularly, to mixed-potential sensors for the detection of various oxidizable and reducible gases.

BACKGROUND OF THE INVENTION

Mixed potential sensors are used for the detection of various oxidizable and reducible gases. Oxidizable gases include hydrogen, hydrocarbons, carbon monoxide, nitric oxide, ethanol, and the like, while reducible gases include oxygen, nitrogen dioxide, and the like. Typical sensors utilize an ionic conducting electrolyte, such as yttria stabilized-zirconia (YSZ), and thin film metal and/or metal oxide electrodes, such as platinum (Pt) and perovskite-type oxides. Multiple reduction/oxidation reactions occurring between the gas phase and the electrode/electrolyte interface cause mixed potentials of differing magnitude to develop at the dissimilar electrodes. The selectivity of such sensors is achieved by the proper selection of the metal and metal oxide electrodes, while the stability of the sensor is achieved by the precise control of the surface area of the electrode and the 3-phase interface region (gas-electrolyte-electrode) of the sensor.

The mixed-potential that is developed at an electrode-electrolyte interface in the presence of oxidizable gases, such as CO or hydrocarbons, is fixed by the rates of reduction and oxidation of the oxygen and the oxidizable gas, respectively (Reactions 1 and 2). Carbon monoxide is used here as an example but the theory is also applicable to other oxidizable/reducible gases:

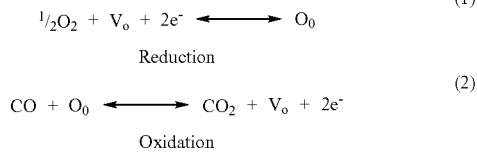

When the kinetic rate for the reduction reaction equals that of the oxidation reaction a stable potential is established. Similar reactions with different kinetics occur on the other electrode triple-phase boundary area. The difference in potential between the electrodes is the device output voltage. The preferred mixed potential CO sensing device consists of an electrode that kinetically inhibits the oxygen reduction reaction yet is fast at CO electro-oxidation and a second electrode that exhibits fast oxygen reduction kinetics yet is poor at CO electrochemical oxidation.

Since the mixed-potential is controlled by the kinetics of various reactions, control of the 3-phase (electrolyte/electrode/gas) area is of importance. Moreover, since the response time of these sensors is fixed by the speed of various reactions, the sensor design is preferably optimized to maximize the rates of reactions 1 and 2.

In the prior art, a dense YSZ electrolyte is used as the substrate and a metal or metal oxide electrode is deposited on top of this electrolyte. The length of the active 3-phase interface is controlled by the morphology of the electrode. A highly porous electrode results in better gas access and greater 3-phase interface, whereas a denser electrode leads to poorer gas access and less 3-phase interface. One drawback of this type of arrangement is that the gas has to meander through the pores of a catalytically active material (the electrode) before reaching the 3-phase interface where the reduction and oxidation reactions occur. Hence, the hydrocarbons (or other reducing gases) are heterogeneously oxidized at the metal (or metal oxide) electrode before they reach the 3-phase interface with the electrolyte, with a concomitant loss in sensor sensitivity and increase in response time.

Mukundan et al. (U.S. Pat. No. 6,656,336, issued Dec. 2, 2003) disclose a non-methane hydrocarbon sensor that measures the amount of hydrocarbons present in an exhaust stream containing oxygen. The selectivity of the device is achieved by the proper selection of the oxide electrode, while the stability of the device is achieved by the precise control of the surface area (SA) of the electrode and the 3-phase interface region (3 PA) (gas-electrolyte-electrode) of the sensor. By controlling the ratio of the SA to the 3PA, the rates of the heterogeneous catalysis and electrochemical catalysis are controlled for any particular electrode used. Thus, by proper selection of the electrode material and electrode dimensions, the magnitude of sensor response to any particular gas species can be amplified (selectivity).

Mukundan et al. (U.S. Pat. No. 6,605,202, issued Aug. 12, 2003) disclose a mixed-potential electrochemical sensor for the detection of gases, such as CO, NO, and non-methane hydrocarbons, in room air. The sensor utilizes a ceria-based electrolyte, and metal wire electrodes. The stability and reproducibility of the sensor is achieved by using wire electrodes instead of the usual thin or thick film electrodes that are currently employed. The metal wire-electrodes are directly embedded into the electrolyte and co-sintered with the electrolyte in order to produce a stable metal/electrolyte interface.

The present invention uses thin film technology to produce a mixed-potential electrochemical sensor for the detection of gases, such as CO, NO, and non-methane hydrocarbons, where the sensor exhibits fast response time, good reproducibility, and can be produced using inexpensive thin film technology.

Bloemer et al. (U.S. Pat. No. 6,352,631, issued Mar. 5, 2002) teach a mixed-potential sensor formed by depositing electrodes on a dense electrolyte, where the electrodes are exposed directly to the gas stream to be sampled. Muller et al. (U.S. Pat. No. 4,277,323) teach an oxygen sensor where two electrodes are put on a porous substrate and completely covered with a thin YSZ film. While this works well for an $O_2$ sensor and improves performance, this will not provide a mixed potential sensor. Further, Mueller et al. provide gas access only through a porous substrate onto an electrode embedded in an electrolyte where the 3-phase interface region is not well defined.

Various objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

In accordance with the purposes of the present invention, as embodied and broadly described herein, the present invention includes a mixed potential sensor for oxidizable or reducible gases and a method of making the mixed potential sensor. A substrate is provided and two electrodes are formed on a first surface of the substrate, each electrode being formed of a different catalytic material selected to produce a differential voltage between the electrodes from electrochemical reactions of the gases catalyzed by the electrode materials. An electrolytic layer of an electrolyte is formed over the electrodes to cover a first portion of the electrodes from direct exposure to the gases with a second portion of the electrodes uncovered for direct exposure to the gases.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings.

DETAILED DESCRIPTION

The sensor design of the present invention provides dense thin film electrodes deposited on an inert substrate in a non-intersecting, preferably parallel, geometry with a second layer of thin film electrolyte that partially covers the two electrode strips. The fabrication of sensors in this manner produces a device with a reproducible triple phase boundary. The triple phase boundary is the region where the gases come in contact with the electrode/electrolyte interface. If the YSZ electrolyte film were 100% dense, then the region is defined by the line at which the YSZ ends and the gas/electrode interface begins. If the YSZ is not completely dense, there is then gas diffusion through the electrolyte to the surface contact between the electrodes and the overlying electrolyte, where the electrode/electrolyte interface forms a triple phase boundary.

The fabrication process also produces a device that does not rely on gas diffusion through porous electrode materials and consequent changes in gas composition from reactions within the electrodes. The end result is a higher signal response and improved device-to-device response reproducibility. Another advantage is that the need for sintering of the electrodes is greatly reduced, as the materials are already dense.

The present devices also offer an advantage over dense electrode structures produced on solid electrolyte substrates. Surprisingly, we have found that dense films deposited onto zirconia electrolyte substrates do not perform as well, nor is the device response as reproducible, as devices where the electrolyte is deposited on top of the electrode material.

Figure 1A:
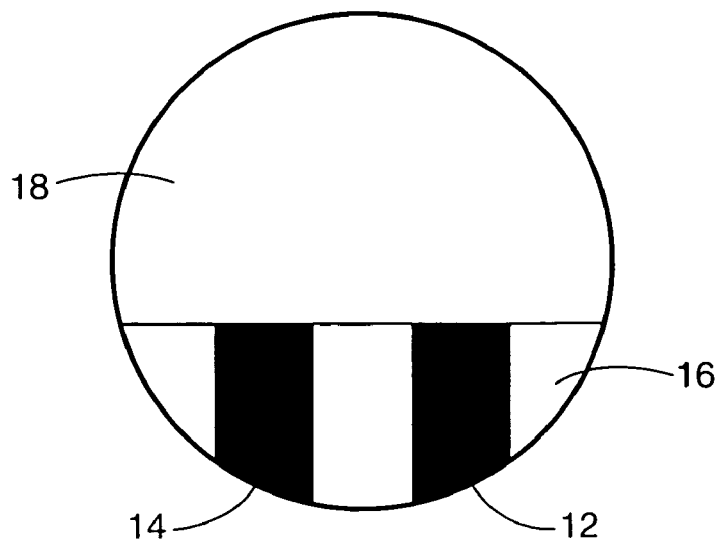
FIGS. 1A and 1B are a partial top view and a side view of one embodiment of a sensor according to the present invention.
Figure 1B:
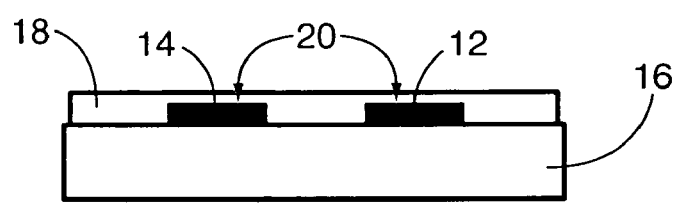
Figure 2:
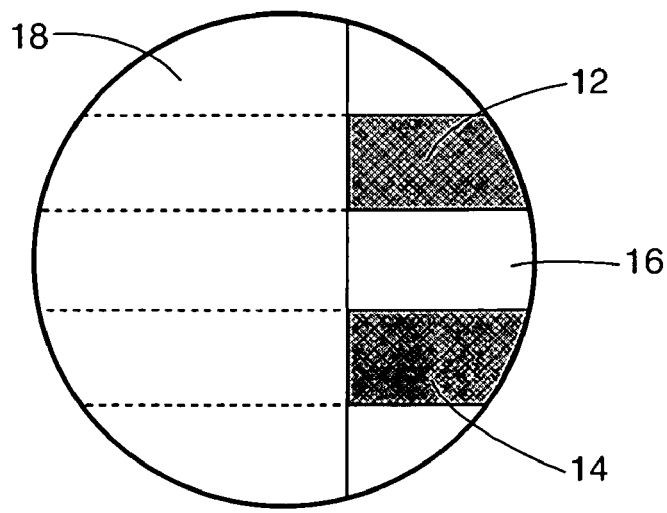
FIG. 2 is a pictorial illustration of a sensor shown in FIGS. 1A and 1B.

A schematic of a sensor configuration according to one embodiment of the present invention is illustrated in FIGS. 1A, 1B, and 2. In the depicted sensor configuration, thin (e.g., 0.5 µm) electrode (metal or metal oxide) films 12, 14 are deposited on a relatively thick (e.g., 0.5 mm) dense substrate 16. Suitable dense substrates include sapphire, YSZ, alumina, MgO, and the like. Electrodes 12, 14 are then partially covered with a thin (e.g., 5-10 µm above substrate 16) electrolyte layer 18. Suitable electrolytes include YSZ, or other zirconia-based or ceria- or bismuth-based electrolytes, or other oxygen ion conducting oxide.

To achieve thin dense films, deposition techniques such as RF magnetron or DC sputter vapor deposition process (for electrodes 12, 14) and electron beam evaporation process (for the yttrium-zirconium oxide solid electrolyte 18) have been used. These processes typically produce thin films having theoretical densities >70% of theoretical density. A well defined 3-phase interface region 20 is formed along the edge of electrolyte 18 where electrodes 12, 14 emerge from beneath electrolyte layer 18 and along the interface surface between electrolyte 18 and electrodes 12, 14.

Exemplary deposition processes are as follows:

RF Magnetron Sputtering

Substrates (either YSZ, sapphire, or alumina) were ultrasonically cleaned in isopropanol or acetone and then dried and fired in air at 1100° C. for several hours. The substrates were then mounted onto a Ni faceplate that was subsequently placed into contact with a boron nitride heater specifically designed for vacuum operation. The substrate was typically held to the Ni faceplate by an alumina mask held by a metal clip or the substrate could be glued to the faceplate using a water-based, silver epoxy (AREMCO). The substrate temperature was monitored using a type K thermocouple embedded within the Ni faceplate. To measure thickness and deposition rates, a masked piece of polished sapphire was mounted next to the substrate. The step created on this witness sample from the shadow mask was then used to measure the film thickness produced in the PVD run using a DEKTAK profilimeter.

Substrates were mounted to a heater box using silver paint; the nickel heater faceplate temperature was monitored using a thermocouple and/or an IR camera. For the film depositions used in this work, the temperature was maintained at 700° C. The heater assembly was placed into an ultra-high vacuum sputter system with two R.F. magnetron guns. An off-axis source sample geometry was used in the sputtering process. The target material consisted of a mixture of Cr metal, $LaF_3$, and $SrF_2$ or $MgF_2$. The mixture amounts are determined by the desired stoichiometry of the electrode, e.g., $La_{0.8}Sr_{0.2}CrO_3$, or $La_{0.8}Mg_{0.2}CrO_3$. Suitable metal electrode targets include Pt, Pd, and Au. These exemplary electrode configurations are not meant to be limiting, since a person skilled in the art can select any number of electrode configurations based on the sensor environment, desired sensitivity, and the like.

All of the sputter depositions were carried out at a RF power level of 125 W. Typical sputter pressures were between 40 and 45 mTorr of Argon. The films were post-annealed at 1000° C. in a water vapor and argon atmosphere to convert the fluorides to a perovskite oxide. Other known target materials are used as a target material to obtain the metal electrode. X-ray diffraction and electron microprobe analysis confirmed that the films were the desired phase and composition. Film thicknesses were determined by sputtering onto shadow-masked polished sapphire single crystal substrates using identical sputter conditions. The film thickness was measured using a stylus profilometer DEKTAK.

Electron Beam Evaporation

An electrolyte is then deposited over the electrodes by electron beam evaporation. For an exemplary YSZ film, the YSZ source consisted of sheets of Cera-Flex™ brand yttria-stabilized zirconia (YSZ) obtained from Marketech International in 0.5×100×100 mm sheets that were cut into smaller pieces and arranged evenly to fill the electron beam hearth. A series of calibration runs were required first in order to find deposition rates that produced films with the desired thickness. The typical substrate temperature was maintained at 800° C. throughout the run. The heater faceplate (and affixed substrate) was positioned on-axis for the electron beam depositions, 6.5 inches away from the source. A quartz crystal rate monitor was used to control the material deposition rate. Other electrolytes can be deposited by selecting a suitable material source, the selection of which is well known to persons skilled in electron beam evaporation.

Figure 3:
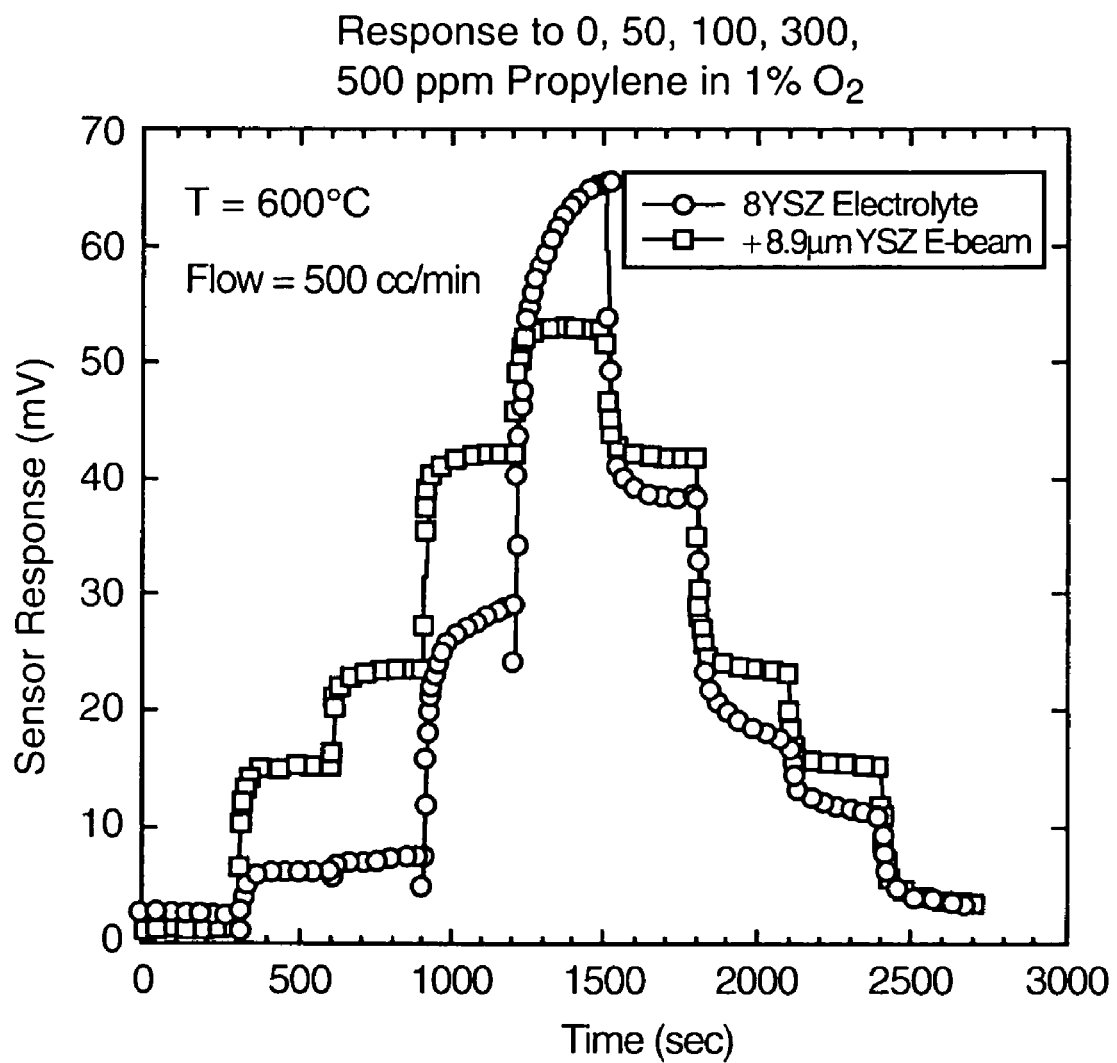
FIG. 3 graphically compares sensor performance without and with a thin electrolyte cover for the electrodes.

The sensor (FIGS. 1A, 1B, and 2) is formed by only partially coating electrodes 12, 14 with a thin film of electrolyte 18, i.e., a first portion of electrodes 12, 14, is covered by electrolyte 18 and not directly exposed to the gas or gases being detected, and a second portion of the electrodes 12, 14 is masked during the deposition of electrolyte 18 and is not covered by electrolyte 18, for direct exposure to the gas or gases. The performance of a sensor with partially coated electrodes is compared to that of a sensor with uncoated electrodes, as shown in FIG. 3. The circles show the response of a sensor with Pt and $La_{0.8}Sr_{0.2}CrO_3$ electrodes sputtered onto a 0.5 mm thick YSZ substrate, while the squares show the response of the same sensor that has now been partially coated with a layer of the electrolyte. The response of the uncoated sensor is very slow and shows some hysterisis (e.g., response to 300 ppm propylene is ≈30 mV when the concentration is increasing and is ≈38 mV when the gas concentration is decreasing). On the other hand, the response of the sensor is significantly improved by the partial YSZ over-coat (8.9 μm). The over-coated sensor shows much faster response times and the hysterisis is completely eliminated. This enhancement in sensor performance may be due to the higher quality (less interfacial reaction) of the triple phase interface produced by the over-coating method.

Figure 4:
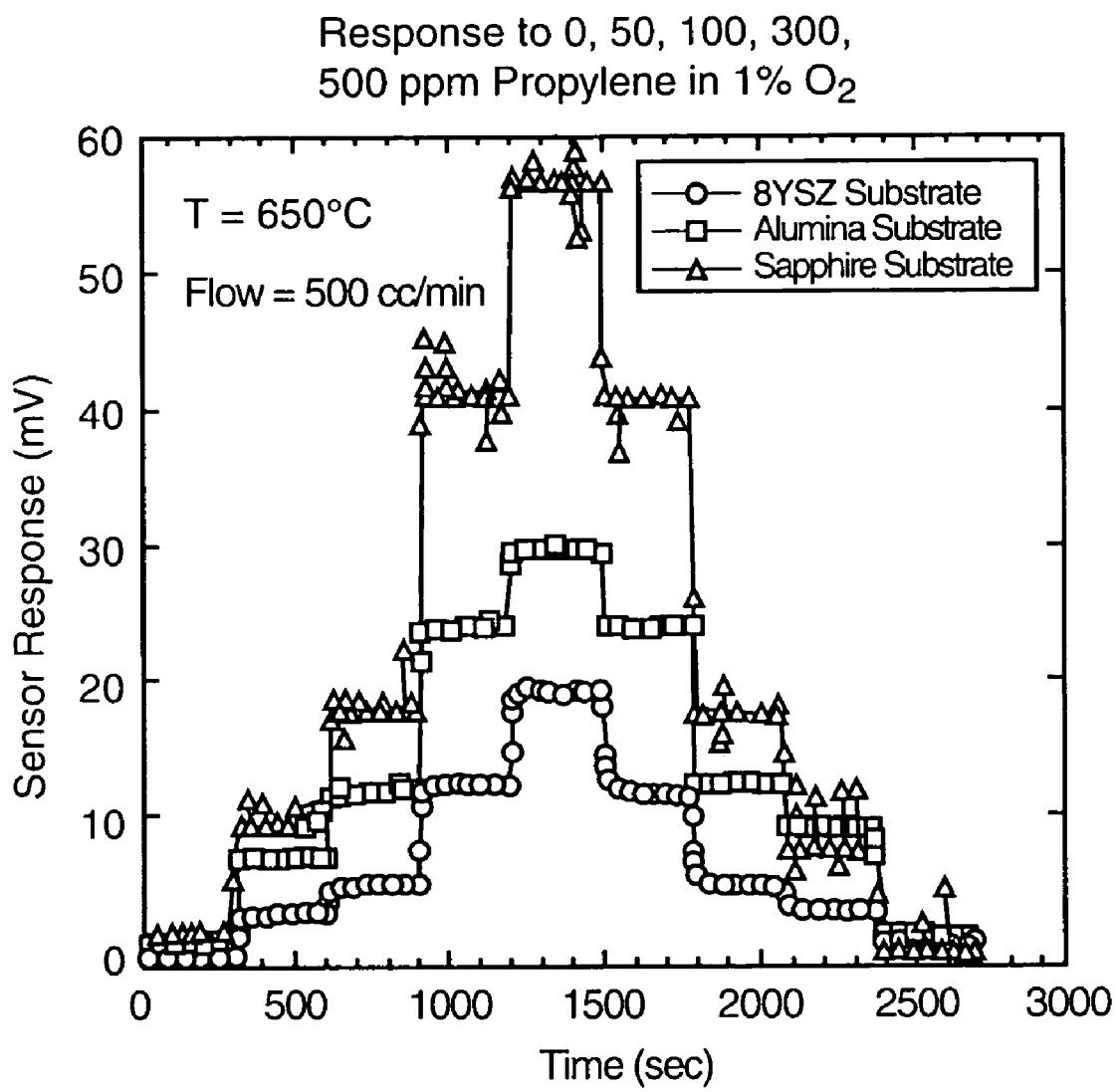
FIG. 4 graphically depicts sensor performance with electrodes on various substrates.

The sensor described herein can be made with most commonly available dense substrates including alumina, sapphire and YSZ. A dense substrate is impermeable to gases (i.e., no open, through porosity) generally where the density is >92-95% of theoretical density. FIG. 4 graphically depicts the propylene response of three sensors having different substrates of YSZ, alumina, and sapphire. The response curves of all these sensors are excellent and the sensor sensitivity is increased either by using more inert or better quality substrates. Sapphire and alumina have the same catalytic activity, but the sapphire substrate provides a smoother surface for higher sensitivity. YSZ and alumina have approximately the same surface quality, but YSZ is more catalytic, so alumina provides better sensitivity. Persons of ordinary skill in the art can make these sensors on other inert and gas impermeable substrates.

Figure 5:
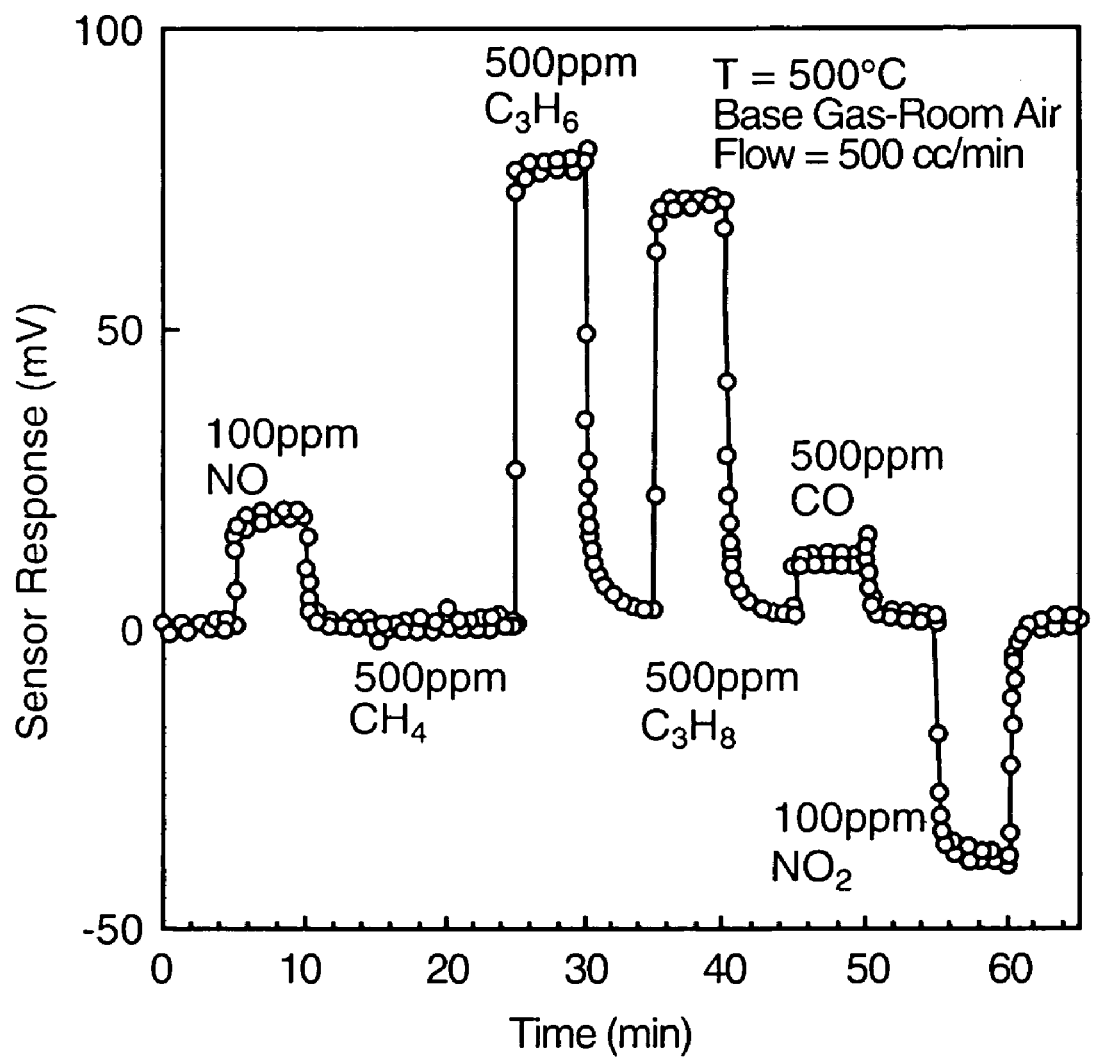
FIG. 5 graphically depicts sensor performance in various oxidizable and reducible gases.

FIG. 5 illustrates the response of a thin film sensor using Pt (0.5 μm) and $La_{0.8}Sr_{0.2}CrO_3$ (2.1 μm thick) electrodes and a 8YSZ electrolyte ($ZrO_2$ doped with 8 mole % $Y_3O_3$, where a suitable doping is in the range 2-10 mole %), 10.6 μm thick, on an alumina substrate. The response is shown for propylene, methane, carbon monoxide and nitrogen dioxide. Note the negative response for the nitrogen dioxide, a reducible gas.

Thus, this configuration has several advantages over common geometries such as parallel electrode on electrolyte and symmetric electrode-electrolyte-electrode devices described in the literature:

a) The triple phase interface area may be precisely controlled by lithographic techniques.
b) The electrolyte film can be made thin and porous to minimize the diffusion distances for the gas species.
c) Because the diffusion distances are short, the non-electrochemical heterogeneous reactions are minimized. The non-electrochemical catalysis by the sensor materials reduces the concentration of gases that can reach the electrochemical interface and thus lowers the mixed potential.
d) The sensors may be produced on common substrates that are not electrolytes such as aluminum oxide or magnesium oxide.
e) The sensors may be miniaturized via photolithographic methods. Multiple sensors that utilize different electrode materials and electrolyte may be patterned on a single wafer.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A mixed potential sensor for oxidizable or reducible gases comprising:
   a substrate;
   two electrodes formed on a first surface of the substrate, each electrode being formed of a different catalytic material selected to produce a differential voltage between the electrodes from electrochemical reactions of the gases catalyzed by the electrode materials; and
   an electrolytic layer of an oxygen ion conducting metal oxide electrolyte formed over the electrodes to cover a first portion of the electrodes from direct exposure to the gases, with a second portion of the electrodes uncovered for direct exposure to the gases.

2. The mixed potential sensor of claim 1, wherein the substrate is an inert, gas impermeable material.

3. The mixed potential sensor of claim 2, wherein the electrodes have a density characteristic of materials deposited by RF magnetron or DC sputter vapor deposition processes.

4. The mixed potential sensor of claim 1, wherein the electrodes have a density characteristic of materials deposited by RF magnetron or DC sputter vapor deposition processes.

5. The mixed potential sensor of any one of claims 1-3, wherein the electrolytic layer is formed to a thickness of 5 μm to 10 μm with a density characteristic of materials deposited by an electron beam evaporation process.

6. The mixed potential sensor of claim 1 wherein said oxygen ion conducting metal oxide electrolyte is selected from yttria stabilized-zirconia, zirconia-based electrolytes, ceria-based electrolytes, or bismuth-based electrolytes.

7. The mixed potential sensor of claim 6 wherein said oxygen ion conducting metal oxide electrolyte is yttria stabilized-zirconia.

8. A method for making a mixed potential sensor for oxidizable or reducible gases comprising:
   providing a gas impermeable substrate;
   forming electrode strips of two different materials effective to produce a differential potential therebetween in electrochemical reactions with one of the oxidizable or reducible gases;
   depositing a thin, dense layer of an oxygen ion conducting metal oxide electrolyte to cover a first portion of the electrodes from direct exposure to the gases while leaving a second portion of the electrodes uncovered for direct exposure to the gases.

9. The method of claim 8, including forming the electrodes by a deposition process selected from the group consisting of RF magnetron vapor deposition or DC sputter vapor deposition.

10. The method of claim 8, including depositing said layer of said oxygen ion conducting metal oxide electrolyte by an electron beam evaporation process.

11. The method of claim 8 wherein said oxygen ion conducting metal oxide electrolyte is selected from yttria stabilized-zirconia, zirconia-based electrolytes, ceria-based electrolytes, or bismuth-based electrolytes.

12. The method of claim 11 wherein said oxygen ion conducting metal oxide electrolyte is yttria stabilized-zirconia.

* * * * *